United States Patent
Day et al.

(10) Patent No.: US 9,814,846 B2
(45) Date of Patent: Nov. 14, 2017

(54) METHOD AND SYSTEM FOR DETERMINING INFORMATION RELATED TO A DRUG RESERVOIR

(75) Inventors: Shane Alistair Day, Warwick (GB); Barry Yates, Kenilworth (GB); Richard James Vincent Avery, Chipping Campden (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1045 days.

(21) Appl. No.: 13/814,492

(22) PCT Filed: Aug. 25, 2011

(86) PCT No.: PCT/EP2011/064629
§ 371 (c)(1),
(2), (4) Date: Apr. 26, 2013

(87) PCT Pub. No.: WO2012/025590
PCT Pub. Date: Mar. 1, 2012

(65) Prior Publication Data
US 2013/0226139 A1    Aug. 29, 2013

Related U.S. Application Data

(60) Provisional application No. 61/377,128, filed on Aug. 26, 2010.

(30) Foreign Application Priority Data

Oct. 26, 2010    (EP) .................................... 10188858

(51) Int. Cl.
*A61M 31/00*    (2006.01)
*A61M 5/50*    (2006.01)
*G06F 19/00*    (2011.01)

(52) U.S. Cl.
CPC ....... *A61M 5/5086* (2013.01); *G06F 19/3462* (2013.01); *A61M 2205/60* (2013.01)

(58) Field of Classification Search
CPC .... A61M 5/24; A61M 5/3125; A61M 5/5086; A61M 5/16831; A61M 5/172;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| DK | WO 2010092156 A1 * | 8/2010 | .............. A61M 5/24 |
| EP | 0937471 | 8/1999 | |

(Continued)

OTHER PUBLICATIONS

International Search Report for Int. App. No. PCT/EP2011/064629, dated Aug. 29, 2012.

*Primary Examiner* — Kevin C Sirmons
*Assistant Examiner* — Tiffany Legette-Thompson
(74) *Attorney, Agent, or Firm* — McDonnell Boehnen Hulbert & Berghoff LLP (57) ABSTRACT

Disclosed herein are methods and systems for detecting information related to a drug reservoir. According to one example disclosed herein, a method includes a detector feature determining an electrical property related to a coded material for a drug reservoir, wherein the coded material comprises at least one circuit. The at least one circuit may be printed onto the drug reservoir. The method further includes determining information related to the drug reservoir based at least on the determined electrical property.

18 Claims, 7 Drawing Sheets

(58) Field of Classification Search
CPC .......... A61M 2205/60; A51M 2205/60; A51M 2205/33; G06F 19/00; G06F 19/344; G06F 19/30; G06F 19/3462; A61J 1/18; A61J 2205/00; A61J 2205/10; A61J 2205/60
USPC .......... 604/65, 189, 404; 340/10.1; 235/375
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,435,076 A * | 7/1995 | Hjertman | A61M 5/284 206/219 |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0032429 A1 * | 3/2002 | Hjertman | A61M 5/145 604/500 |
| 2002/0052578 A1 | 5/2002 | Moller | |
| 2002/0120235 A1 | 8/2002 | Enggaard | |
| 2003/0006209 A1 | 1/2003 | Stefen et al. | |
| 2003/0050609 A1 | 3/2003 | Sams | |
| 2003/0055685 A1 | 3/2003 | Cobb et al. | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0107899 A1 * | 5/2005 | Steffen | A61M 5/172 700/90 |
| 2005/0113765 A1 | 5/2005 | Veasey et al. | |
| 2006/0153693 A1 | 7/2006 | Fiechter et al. | |
| 2007/0197968 A1 * | 8/2007 | Pongpairochana | A61M 5/20 604/131 |
| 2009/0043253 A1 * | 2/2009 | Podaima | G06F 19/322 604/67 |
| 2009/0275916 A1 | 11/2009 | Harms et al. | |

FOREIGN PATENT DOCUMENTS

| | | |
|---|---|---|
| EP | 0937476 | 8/1999 |
| EP | 1776975 | 4/2007 |
| WO | 99/38554 | 8/1999 |
| WO | 01/10484 | 2/2001 |
| WO | 01/58236 | 8/2001 |
| WO | 2007/041843 | 4/2007 |
| WO | 2009/015933 | 2/2009 |
| WO | 2010/092156 | 8/2010 |

* cited by examiner

Low pass filter

FIG. 13A

High pass filter

FIG. 13B

METHOD AND SYSTEM FOR DETERMINING INFORMATION RELATED TO A DRUG RESERVOIR

CROSS REFERENCE TO RELATED APPLICATIONS

The present application is a U.S. National Phase Application pursuant to 35 U.S.C. §371 of International Application No. PCT/EP2011/064629 filed Aug. 25, 2011, which claims priority to U.S. Provisional Patent Application No. 61/377,128 filed Aug. 26, 2010 and European Patent Application No. 10188858.4 filed Oct. 26, 2010. The entire disclosure contents of these applications are herewith incorporated by reference into the present application.

FIELD OF THE INVENTION

Specific embodiments of the present disclosure relate to a method and system for determining information related to a drug reservoir, particularly a drug reservoir containing a medicament. As just one example, such medicament reservoirs may comprise an ampoule, a cartridge, or a vial and may be used with a medical delivery device. Such exemplary medical delivery devices could comprise a syringe, a pen type syringe, a pump, or other similar device that requires a reservoir containing at least one medicament.

BACKGROUND

The present disclosure is generally directed to reservoirs, particularly reservoirs containing a medicament. More particularly, the present disclosure is generally directed to determining information related to a drug reservoir, which may help ensure that a delivery device can only be used with a drug reservoir for which it is intended. As just one example, such medicament reservoirs may comprise an ampoule, a cartridge, a vial, or a pouch, and may be used with a medical delivery device. Exemplary medical delivery devices include, but are not limited to syringes, pen type injection syringes, credit-card-shaped injection devices, pumps, inhalers, or other similar injection or infusing devices that require at least one reservoir containing at least one medicament.

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user may dispose of the empty cartridges properly. Where the drug delivery device comprises a disposable device, once the cartridge is empty, the user may be recommended to dispose of the entire device.

Such known self administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining whether the medicament contained in the cartridge is indeed the correct type of medicament to be administered by the patient. Alternatively, certain known drug delivery devices do not present a mechanism for determining whether the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g. 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

One problem to be solved by the present invention is to provide a medical delivery device and a method where the safety of the user is increased.

SUMMARY

One aspect relates to a method of determining information related to a drug reservoir. The method may comprise a detector feature determining an electrical property related to the drug reservoir, in particular to a coded material for the drug reservoir. The coded material may comprise at least one circuit. The at least one circuit may be an RCL circuit. The at least one circuit may comprise at least one fused conductor. The method further may include determining information related to the drug reservoir based at least on the determined electrical property.

The method may be used for test purposes. In particular, the method may be applicable for non-therapeutic and/or non-surgical purposes.

According to an embodiment, the coded material for the drug reservoir is disposed on a location selected from the group consisting of a location on the drug reservoir, a location on a label of the drug reservoir, a location on a holder of the drug reservoir, a location on a box of the drug reservoir, a location on a security wrapping of the drug reservoir, and a location on a blister pack of the drug reservoir.

According to an embodiment, at least one component of the at least one circuit is printed onto the drug reservoir.

According to an embodiment, the method further comprises the step of determining a second electrical property of the at least one circuit. Based on the second property, information, in particular further information, related to the drug reservoir may be determined.

According to an embodiment, the detector feature comprises an oscillator. The determined electrical property may comprise at least one of a resonant frequency of the at least one circuit and an attenuation of the at least one circuit.

According to an embodiment, the at least one circuit comprises a low-pass filter. Alternatively, the at least one circuit may comprise a high-pass filter. The determined electrical property may comprise at least one of a frequency passed and a frequency blocked.

According to an embodiment, the at least one circuit is a single-layer circuit. Alternatively, the at least one circuit may be a double-layer circuit.

According to an embodiment, the detector feature comprises an electrical connector. The detector feature may comprise a plurality of connectors. The electrical connector may be a contact, in particular a metal contact. Alternatively, the electrical connector may be a contactless electrical connector.

According to an embodiment, the information related to the drug reservoir is information selected from the group consisting of drug type, drug concentration, a manufacturing date of the reservoir, an expiration date of the drug, and a storage condition of the drug. The step of determining information related to the drug reservoir may be performed as a user loads the drug reservoir in a drug delivery device.

According to an embodiment, the method further comprises the step of, based on the determined information, determining that the drug reservoir is not intended for use with the drug delivery device.

According to an embodiment, the method further comprises displaying an indication that the drug reservoir is not intended for use with the drug delivery device.

According to an embodiment, the method further comprises preventing insertion of the drug reservoir into the drug delivery device. Preventing insertion of the drug reservoir may comprise activating an electronic latch that prevents insertion of the drug reservoir.

According to an embodiment, the method further comprises identifying the drug reservoir based on the information.

According to an embodiment, the drug reservoir is inserted in a drug delivery device. The method may further comprise controlling dose selection based on the identified drug reservoir. Controlling dose selection based on the identified drug reservoir may comprise preventing dose selection when the identified drug reservoir is not intended for use with the drug delivery device. Additionally or alternatively, controlling dose selection based on the identified drug reservoir may comprise setting a maximum dose. Additionally or alternatively, controlling dose selection based on the identified drug reservoir may comprise setting a minimum dose. Additionally or alternatively, controlling dose selection based on the identified drug reservoir may comprise controlling the dosing frequency.

According to an embodiment, the drug reservoir is inserted in a drug delivery device. The method further may comprise controlling dispensing of the drug based on the identified drug reservoir. Controlling dispensing of the drug based on the identified drug reservoir may comprise preventing dispensing of the drug when the identified drug reservoir is not intended for use with the drug delivery device. Additionally or alternatively, controlling dispensing of the drug based on the identified drug reservoir may comprise controlling at least one of a dispense speed and a required dispense force.

A further aspect relates to a medical delivery device. The medical delivery device may comprise a drug reservoir holder. The drug reservoir holder may be operable to receive a drug reservoir. The medical delivery device may comprise a detector. The detector may comprise a connector. The detector may comprise a processor. The detector may comprise data storage comprising instructions executable by the processor. The drug delivery device may be configured to perform the previously described method.

A further aspect relates to a medical delivery device. The device may be capable of determining information related to a drug reservoir. The medical delivery device may include a drug reservoir holder. The drug reservoir holder may be operable to receive a drug reservoir. The medical delivery device may also include a detector. The detector may be for detecting information related to the drug reservoir. The detector may include a connector. The detector may include a processor. The detector may include data storage. The detector may be operable to determine an electrical property related to the drug reservoir. In particular, the data storage may comprise instructions executable by the processor to determine an electrical property related to the drug reservoir, in particular to a coded material for the reservoir. The coded material may include at least one circuit. The at least one circuit may be an RCL circuit. The detector may be operable to determine information related to the drug reservoir based at least on the determined electrical property. In particular, the instructions may also be executable by the processor to determine information related to the drug reservoir based at least on the determined electrical property.

According to an embodiment, the medical delivery device comprises a display. The display may be configured to display at least a portion of the information related to the drug reservoir.

According to an embodiment, at least one component of the at least one circuit is printed onto the drug reservoir.

According to an embodiment, the detector feature comprises an oscillator. The determined electrical property may comprise at least one of a resonant frequency of the at least one circuit and an attenuation of the at least one circuit.

According to an embodiment, the at least one circuit comprises a low-pass filter. Alternatively, the at least one circuit may comprise a high-pass filter. The determined electrical property may comprise at least one of a frequency passed or blocked.

According to an embodiment, the detector feature comprises an electrical connector. The electrical connector may be a contact, in particular a metal contact. Alternatively, the electrical connector may be a contactless electrical connector.

According to an embodiment, the drug reservoir is selected from the group consisting of a drug cartridge and a drug pouch.

According to an embodiment, after a user attempts to load the drug reservoir into the drug delivery device, the instructions are further executable by the processor to, based on the determined information, determine that the drug reservoir is not intended for use with the drug delivery device.

According to an embodiment, the instructions are further executable by the processor to display an indication that the drug reservoir is not intended for use with the drug delivery device.

According to an embodiment, the instructions are further executable by the processor to prevent insertion of the drug reservoir into the drug delivery device.

According to an embodiment, the instructions are further executable by the processor to identify the drug reservoir based on the determined information related to the drug reservoir.

According to an embodiment, the instructions are further executable by the processor for controlling dose selection based on the identified drug reservoir. Controlling dose selection may comprise preventing dose selection. Additionally or alternatively, controlling dose selection may comprise setting a maximum dose.

According to a preferred embodiment, a method of determining information related to a drug reservoir is provided, the method comprising a detector feature determining an electrical property related to a coded material for the drug reservoir, wherein the coded material comprises at least one circuit, and based at least on the determined electrical property, determining information related to the drug reservoir.

According to a preferred embodiment, a medical delivery device is provided comprising a drug reservoir holder operable to receive a drug reservoir and a detector for detecting information related to the drug reservoir, the detector being configured to be operable to determine an electrical property related to a coded material for the drug reservoir, wherein the coded material comprises at least one circuit and, based at least on the determined electrical property, to determine information related to the drug reservoir.

According to a preferred embodiment, a method of determining information related to a drug reservoir is provided, the method comprising a detector feature determining an electrical property related to a coded material for a drug reservoir, wherein the coded material comprises at least one circuit. The method comprises based at least on the determined electrical property, determining information related to the drug reservoir.

According to a preferred embodiment, a medical delivery device is provided comprising a drug reservoir holder operable to receive a drug reservoir. The medical delivery device comprises a detector for detecting information related to the drug reservoir. The detector comprises a connector, a processor, data storage comprising instructions executable by the processor to determine an electrical property related to a coded material for a drug reservoir, wherein the coded material comprises at least one circuit, and based at least on the determined electrical property, determine information related to the drug reservoir.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

The disclosed method and system may allow for identifying information related to a drug reservoir by an electronic means. The proposed system and method may help a user to distinguish between medicament reservoirs, thereby ensuring that a medical delivery device can only be used with a medicament reservoir for which it is intended. In an arrangement, a given medical delivery device or drug delivery device may be intended to only be used with a single drug reservoir. Thus, the disclosed system and method may help a user to ensure that only the single given drug reservoir is used with the given drug delivery device. However, in other arrangements, a given drug delivery device may be intended for use with multiple drug reservoirs. Thus, the disclosed system and method may help a user to ensure that only the intended reservoirs are used with the drug delivery device.

In addition to allowing a user to identify whether a given drug reservoir is intended to be used with a drug delivery device, the disclosed system and method may also inform a user (or, more generally, any individual dealing with drug reservoirs in any capacity, such as manufacture, shipping, storage, etc.) of other useful information regarding the drug reservoir, such as required storage conditions for the reservoir and/or expiration date of the reservoir. In accordance with the present disclosure, information regarding the drug reservoir may be determined by determining an electrical property related to a coded material by using a detector feature. A method and system for identifying information related to the drug reservoir are described in greater detail below in the following subsections.

Figure 1:
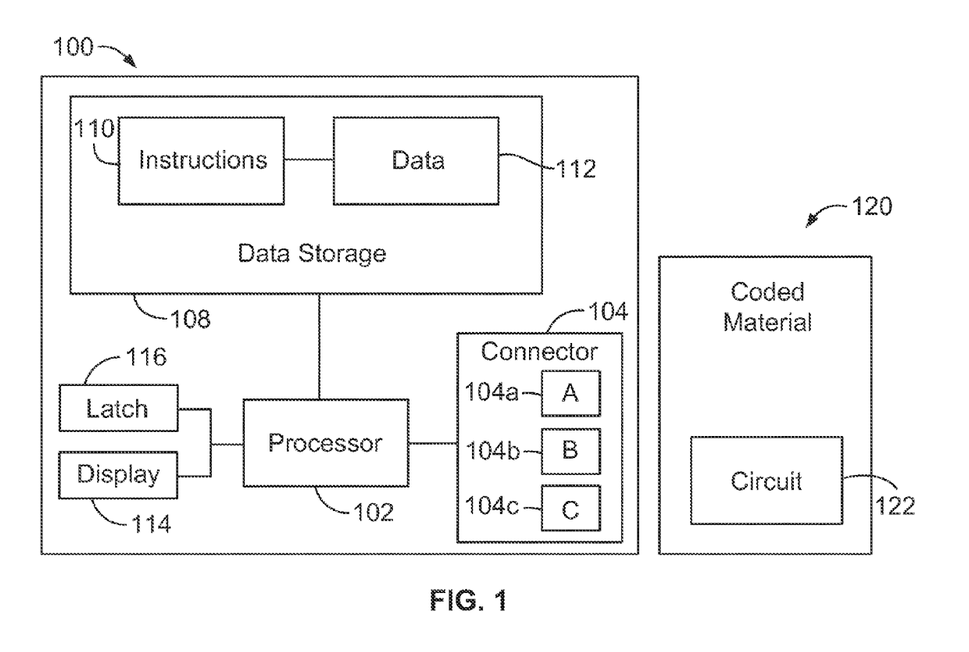
FIG. 1 illustrates an example detector feature.

FIG. 1 depicts a system or detector feature 100 for determining information related to a coded material. This system 100 may determine information related to a drug reservoir. System 100 includes a processor 102 and a connector 104. The system 100 may also comprise data storage 108 comprising instructions 110 executable by the processor 102 to carry out the functions described herein. The processor 102 may comprise a single processor such as a general purpose microprocessor or multiple (e.g. parallel) processors. The data storage 108 may take various forms, in one or more parts, such as a non-volatile storage block and/or a removable storage medium. Data storage 108 may also include data 112, which may be used for carrying out the functions described herein.

In accordance with the proposed system and method, system 100 may be provided on or in a drug delivery device, such as syringes, pen-type injection syringes, credit-card-shaped injection devices, pumps, inhalers, or other similar injection or infusing devices that require at least one reservoir containing at least one medicament. For example, system 100 may be provided in drug delivery device 300 shown in FIG. 3A.

Figure 3A:
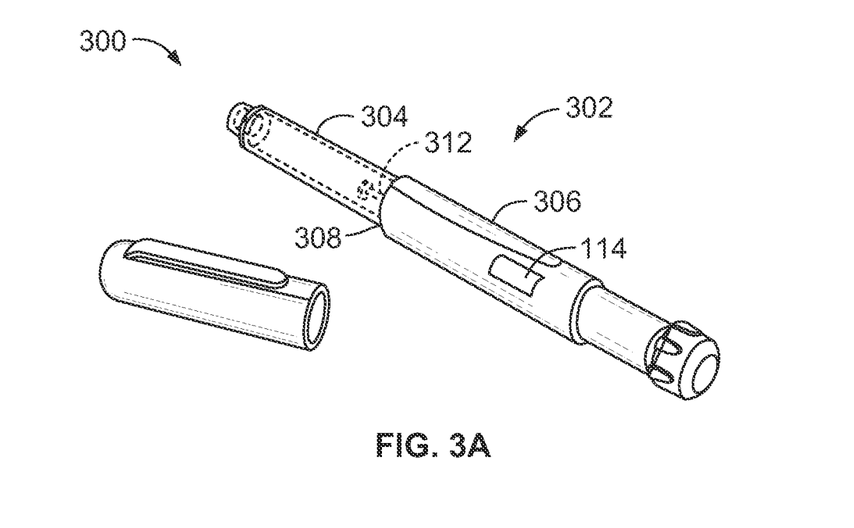
FIG. 3A illustrates a typical pen type drug delivery device that may include the system of FIG. 1.

Referring to FIG. 3A, there is shown the drug delivery device 300. The drug delivery device 300 comprises a housing 302 having a first reservoir retaining part 304, and second main (exterior) housing part 306. Housing part 306 may include a dose setting mechanism. A first end of the reservoir retaining part or cartridge holder 304 and a second end of the main housing 306 are secured together by retaining features 308. In this illustrated arrangement, the reservoir retaining part 304 is secured within the second end of the main housing 306. The pen type syringe may comprise a re-usable or a disposable pen type syringe. Where the syringe comprises a re-usable device, the cartridge holder 304 and the dose setting mechanism are removably coupled together. In a disposable device 300, they are permanently coupled together.

Figure 3B:
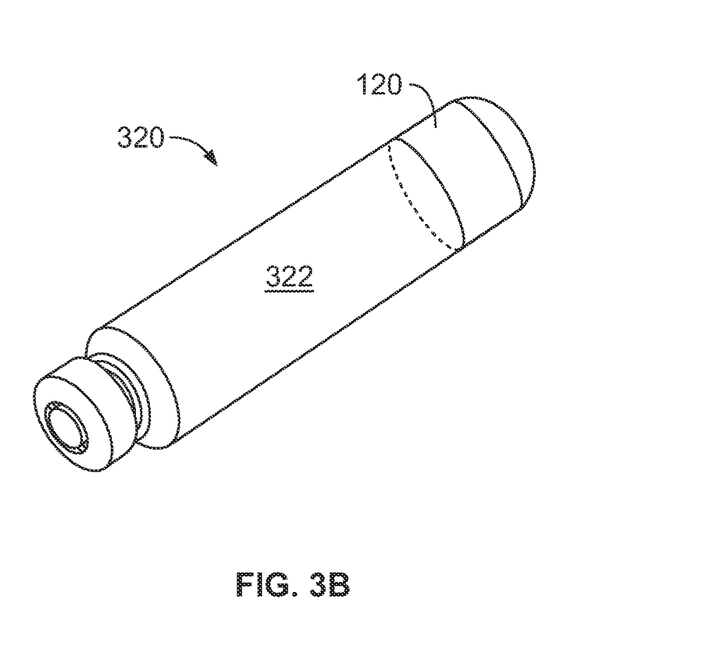
FIG. 3B illustrates an example drug reservoir that may include a coded material having a circuit.

A drug reservoir such as drug reservoir 320 shown in FIG. 3B, from which a number of doses of a medicinal product 322 may be dispensed, may be inserted in the reservoir retaining part 304. Preferably, the drug reservoir 320 contains a type of medicament or medicinal product 322 that must be administered often, such as once or more times a day. One such medicament 322 is insulin.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In one embodiment, the system 100 is provided at or near the interface between the reservoir retaining part 304 and the main housing part 306. Thus, when a drug reservoir 320 is inserted in the drug delivery device 300, the system 100 may detect information related to the reservoir 322 being inserted. In other embodiments, system 100 may be provided at other locations on or in drug delivery device 300. For instance, system 100 may be provided within reservoir retaining part 304 near the distal end of the drug delivery device 300.

As mentioned above, the system 100 may operate to identify information related to drug reservoir 320. Specifically, system 100 may operate to identify information related to the drug reservoir 320 by first identifying a coded material, such as coded material 120 (see FIG. 1) disposed on drug reservoir 320. Coded material 120 includes at least one circuit element 122 having a predefined electrical property or properties that can be detected by system 100. As described in greater detail below, the coded material 120 can be applied to a reservoir such as a cartridge, vial, ampoule, pouch, or container. This coded material 120 may serve to indicate information about the drug reservoir the coded material is disposed on. In an example embodiment, the coded material 120 is disposed directly on a drug reservoir, such as drug reservoir 320 depicted in FIG. 3B. As shown, coded material 120 is disposed near the proximal end of drug reservoir 320. However, in other embodiments the coded material 120 may be disposed elsewhere, perhaps near the distal end of drug reservoir 320. In a given example, the circuit 122 may be printed on or otherwise formed on the coded material 120. The coded material 120 may then be attached to the drug reservoir 320. However, in other examples, the circuit 122 itself may be the coded material. For instance, the circuit 122 may be printed or otherwise formed on a label for the drug reservoir 320 prior to the label being attached to the reservoir 320.

Figure 2:
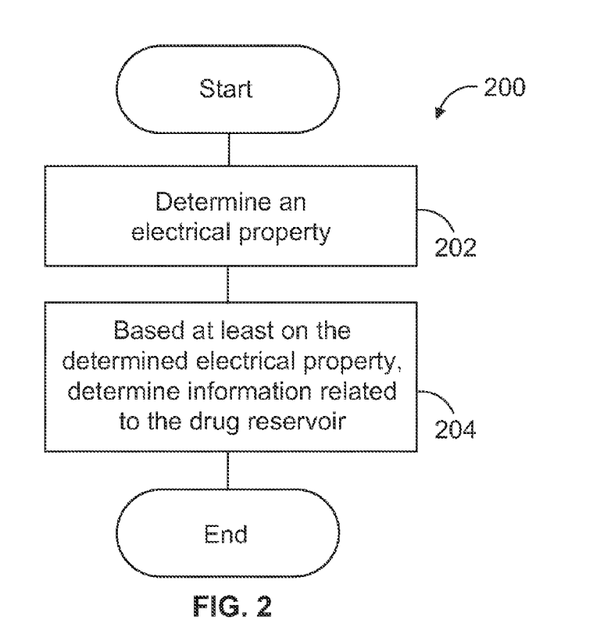
FIG. 2 illustrates an exemplary method of determining information related to a drug reservoir.

FIG. 2 is a flowchart of an exemplary method that may be carried out by detector feature 100, in accordance with an exemplary embodiment. As shown in FIG. 2, method 200 begins at step 202, where system or detector feature 100 determines an electrical property related to the circuit 122 of coded material 120. Then, at step 204, based on the determined electrical property, detector feature 100 determines information related to the drug reservoir 320. These steps are further explained in the following subsections.

Step 202 may occur at various stages. For example, the detector feature 100 may determine an electrical property of the coded material 120 before, during, or after the drug reservoir 320 is inserted into a drug delivery device 300.

In accordance with the disclosed method and system, the connector 104 may communicate with the circuit 122 of the coded material 120, so system 100 may determine an electrical property of the coded material 120. In order to communicate with the circuit 122, the connector 104 may be electrically connected to or otherwise coupled with circuit 122. Further, in given embodiments, the connector 104 may comprise a plurality of different connectors, such as connectors 104*a-c*, that each serve to provide a different connection to the coded material 120. As described above, the coded material 120 is preferably disposed on a drug reservoir, such as drug reservoir 320 depicted in FIG. 3B. For example, the coded material 120 may be on the reservoir, ferrule, bung, label, connector or an adaptor. However, in other given embodiments, the coded material 120 may be disposed elsewhere, such as on the box of a drug reservoir 320 or drug reservoirs 320.

Figure 4:
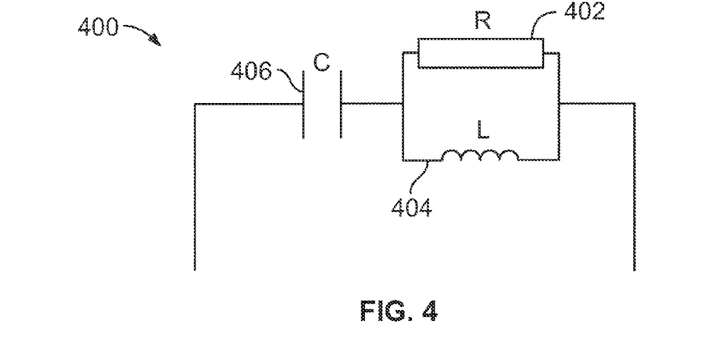
FIG. 4 illustrates an example circuit of a coded material.

When the system or detector feature 100 communicates with the coded material 120, the detector feature 100 may determine an electrical property or electrical properties of the circuit 122. The circuit 122 may be manufactured and designed so as to have a given, predetermined electrical property or electrical properties that can be detected by system 100. As such, the circuit 122 may be any type of circuit with a predetermined electrical property that can be detected, such as any RCL circuit. An example RCL circuit 400 is depicted in FIG. 4. Circuit 400 includes a resistor 402, an inductor 404, and a capacitor 406. As is known in the art, the resistor 402, inductor 404, and capacitor 406 may be selected and arranged in order to yield a predetermined electrical property, such as a predetermined resistance, a predetermined capacitance, and a predetermined inductance. An RCL circuit in accordance with the present disclosure may include any combination of resistors 402 (R), capacitors 404 (C), and/or inductors 406 (L) (i.e. RCL, RC, RL, CL, R, C, or L). Beneficially, different circuits 122 having different electrical properties may each identify different drug reservoirs 320 or different information about a given drug reservoir 320 or reservoirs 320.

As mentioned above, the various components of the circuit 322 may be printed onto the drug reservoir 320 or onto a label to be attached to the drug reservoir 320. The printing may be accomplished by numerous circuit printing methods now known in the art or later developed. For example, the printing method may be a screen-printing method or an ink-jet printing method. Contacts or circuit tracks can be printed using silver-loaded ink, and resistors 402 can be printed using carbon in the ink. If the circuit 122 includes both capacitors 406 and inductors 404, the circuit 122 may need to be printed in two or more layers. Multiple circuit layers may be achieved by covering the first layer of print with a printed insulator, with holes in the printed-insulator layer to allow for connections between circuit layers. A second conductive layer may then be printed on top of the printed-insulator layer.

The connection of the detector feature 100 to the coded material 120 and, more specifically, to the circuit 122 may be made in various ways. For example, connector 104 may be any electrical connector. As an example, connector 104 may be a sprung metal contact. Additionally or alternatively, the connector 104 may include a plurality of sprung metal contacts. In other examples, the connector 104 may be a contactless connector. For instance, the connector 104 may act as a contactless connector through magnetic induction, capacitive coupling, or radio frequency (RF).

Figure 7:
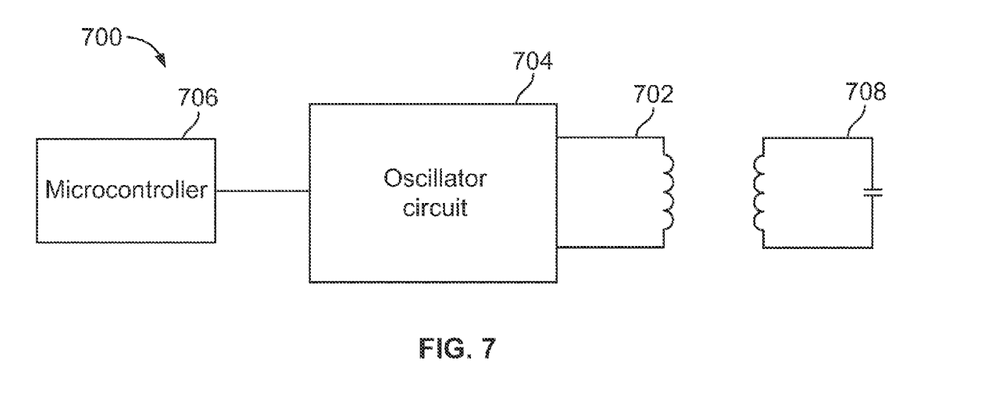
FIG. 7 illustrates an example connector of a detector feature and an example coded material.

An example contactless connector that uses magnetic induction to connect with the coded material is shown in FIG. 7. In particular, system or detector feature 700 includes a connector 702 that is in communication with an oscillator circuit 704. The oscillator circuit 704 is controlled by a controller 706. This system 700 may determine electrical properties of a coded material 708 without physically connecting to the coded material 708. Beneficially, a contactless connector 702 may increase robustness and/or reduce the need to align the coded material 708 with the system 700. By not requiring physical connection, the detector feature 700 may operate to determine an electrical property of the circuit of the coded material 708 even without being aligned to be adjacent to the circuit, as may be required in the case of a sprung metal contact.

Figure 5:
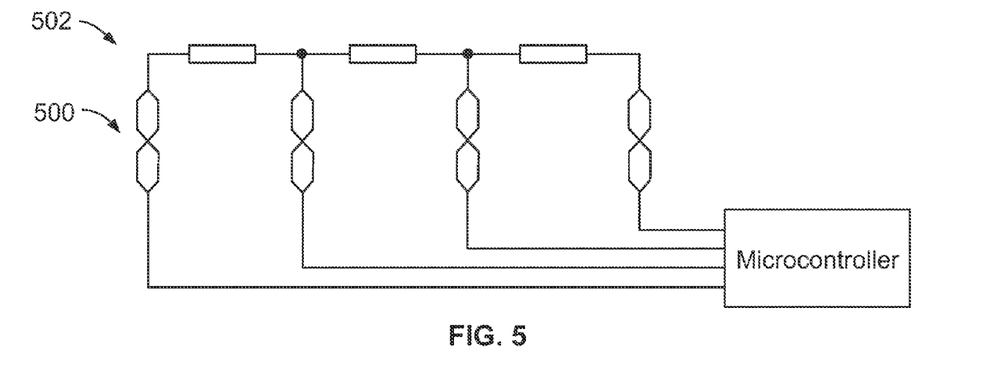
FIG. 5 illustrates an example decoding circuit of a detector feature.

Coding of information by way of drug reservoirs may be achieved in numerous ways. For example, as mentioned above, coding may be achieved by measurement of the resistance, capacitance, and/or inductance between each connector. Measurement of the resistance, capacitance, and/or inductance between each connector may be achieved by, for example, utilizing an analog-to-digital converter connected to a microcontroller or other processor. FIG. 5 depicts a detector feature 500 including an analog-to-digital converter connected to a microcontroller that may be used to determine an electrical property or properties of coded material 502.

Figure 6:
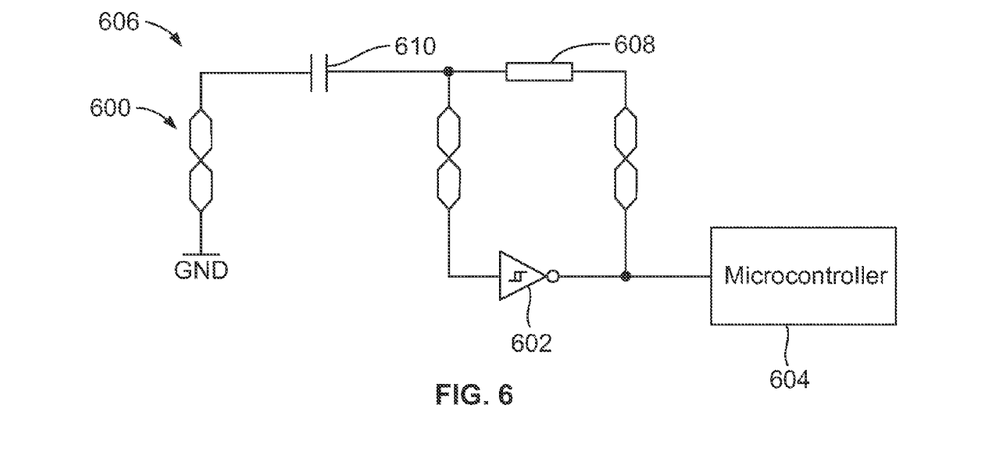
FIG. 6 illustrates another example decoding circuit of a detector feature.

As another example, the system may include an oscillator allowing measurement of the resonant frequency or attenuation of a given circuit. FIG. 6 depicts a detector feature 600 that includes an oscillator formed by a capacitor 610 and a resistor 608, with an inverter 602 and a microcontroller 604. The detector feature 600 may determine information about a coded material 606. In the example of FIG. 6, the resistor 608 and the capacitor 610 on the 606 coded material of a given drug reservoir tune the oscillator circuit of the detector feature 600. The determined information about the coded material 606 may then be decoded with the low-cost microcontroller 604 in order to determine an electrical property or properties of the coded material 606.

Figure 13A:
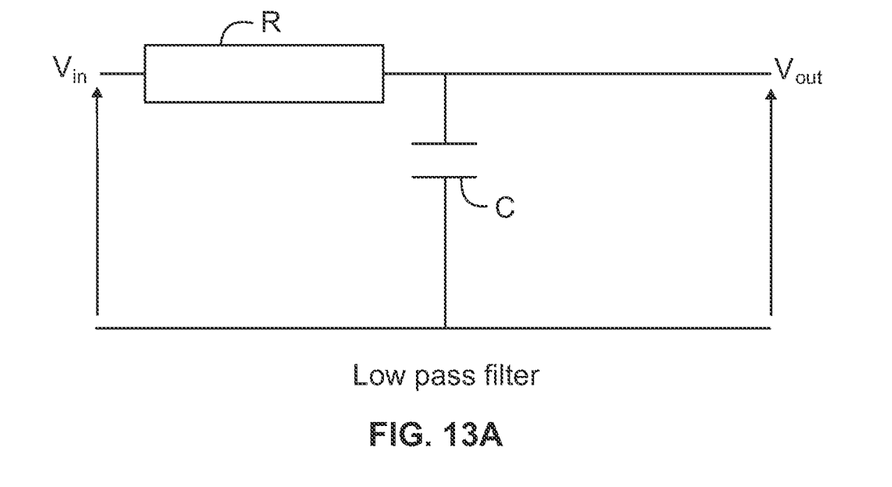
FIG. 13A illustrates an example circuit of a coded material.
Figure 13B:
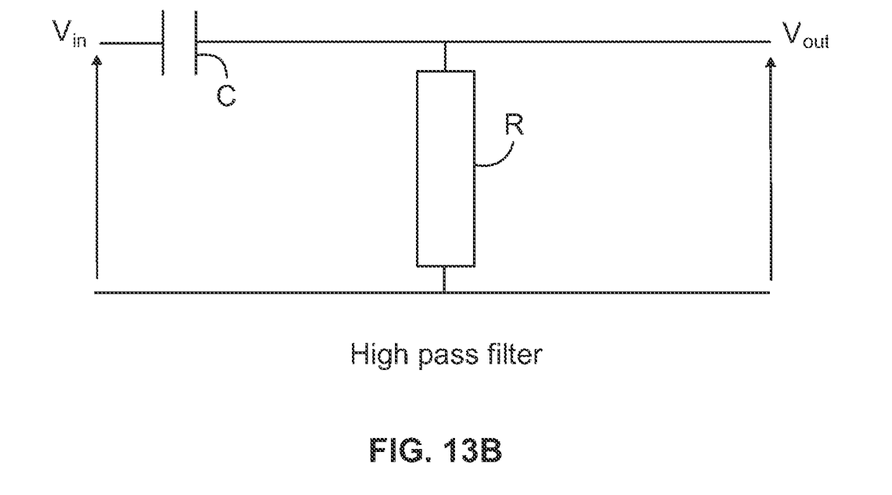
FIG. 13B illustrates another example circuit of a coded material.

As yet another example, the circuit may include a low-pass filter(s) or a high-pass filter(s), allowing measurements of the frequencies passed or blocked. Resistors and capacitors in the coding material can be arranged to form a low pass filter shown in FIG. 13A, or a high pass filter shown in FIG. 13B. Connectors can be arranged so that an input voltage Vin can be applied, and an output voltage Vout can be measured.

Other example measurements that a detector feature may make to determine given electrical properties of a circuit are possible as well.

Based on the determined electrical property, the system 100 may then determine information related to the drug reservoir 320. For instance, the electrical property or properties of the circuit 122 or circuits of the coded material 120 may vary for different types of drug reservoirs, and various electrical properties may be associated with various information related to drug reservoirs. As a particular example, a first given coded material having a first given electrical property (e.g. a first resistance) may be associated with a first drug reservoir. A second given coded material having a second given electrical property (e.g. a second resistance) may be associated with a second drug reservoir. Further, a third coded material having a third given electrical property (e.g. a given capacitance) may be associated with a third drug reservoir, and so forth.

As discussed above, system 100 may comprise data storage 108 that includes data 112. This data 112 may comprise a database of information that links a plurality of electrical properties to respective information regarding a given drug reservoir. For example, the database may include information that links a given electrical property to a type of drug the drug reservoir contains. In addition to identifying a type of drug or drug reservoir, the electrical property of the coded material may serve to identify other information about a drug reservoir. For example, the information related to the drug reservoir may be information related to drug type, a drug concentration, a manufacturing date of the reservoir, an expiration date of the drug, and a storage condition of the drug (e.g. required storage temperature). Other types of information about a drug reservoir are possible as well.

In accordance with the disclosed method and system, a large amount of information may be coded (e.g. distinguishing a large number of medicament reservoirs) by varying the electrical property or properties of the coded material or coding features disposed on the drug reservoir. For instance, multiple materials may be provided on a drug reservoir in order to provide coding for drug reservoirs. For example, three circuits each having a unique electrical property may be provided.

In some embodiments, additional informational coding may be achieved in various ways. For instance, the position of the coded material may also be used for identification purposes. For example, position of the coded material 120 relative to a standard feature may be used to identify information about the drug reservoir 320. As such, system 100 may be further configured to detect the position of the coded material 120. As an example, the axial length of the coded material 120 from a proximal end of the reservoir 320 may provide information related to the drug reservoir 320.

In alternative embodiments, the system 100 may identify coded material 120 based on the size (e.g. the axial, circumferential, and/or radial extent of the coded material) or orientation (e.g. axial strips, circumferential rings, or 2D pattern) of the coded material 120. Alternatively, the number of circuits 122 incorporated within the coded material 120 may also convey information about the drug.

Since information regarding the drug reservoir 320 may be detected during or after a drug reservoir 320 is inserted into a drug delivery device 300, the method and system 100 may react to the identified information at various stages in an operating sequence of the drug delivery device 300. Specifically, system 100 may be configured to take certain actions when a drug reservoir 320 is identified. For instance, the system 100 may react to the information and take an appropriate action during (i) loading of the device 300, (ii) dose selection, and/or (iii) dispensing of the drug. Other stages are possible as well. Beneficially, during these steps, the system 100 may help a user identify whether the drug reservoir 320 being loaded or that is already loaded is intended for the drug delivery device 300.

The step of determining information related to the drug reservoir 320 may be performed as a user loads the drug reservoir 320 in drug delivery device 300. System 100 may identify an electrical property of circuit 122 of the coded material 120 and, then, may determine, based on the electrical property, whether the drug reservoir 320 is intended for use with the drug delivery device 300.

In an embodiment, when the drug reservoir 320 is not intended for use with the drug delivery device 300, the system 100 may display an indication that the drug reservoir 320 is not intended for use with the drug delivery device 300. For instance, as shown in FIG. 1, the system 100 may comprise a display feature 114 that is in communication with the processor 102. As an example, display feature 114 could be located on an outer edge of housing 306, as shown in FIG. 3A. This display feature 114 could indicate that the drug reservoir 320 is incorrect. For example, the display feature 114 may display a red dot or red "X" when an incorrect drug reservoir 320 is loaded. The display feature 114 may also operate to indicate when a correct drug reservoir 320 is loaded. For example, the display feature 114 may display a green dot when a correct drug reservoir 320 is loaded. Other types of indications are possible as well, such as an audible indication.

If a user attempts to insert an incorrect reservoir 320 into the drug delivery device 300, the system 100 may operate to prevent the insertion of the drug reservoir 320 into the drug delivery device 300. For instance, preventing insertion of the drug reservoir 320 may comprise activating an electronically-controlled latch, such as latch 116 shown in FIG. 1, which prevents insertion of the drug reservoir 320. System 100 may also be configured to prevent the reset of a spindle, such as spindle 312 shown in FIG. 3A, of a dose setting mechanism of the drug delivery device if the user attempts to load the drug delivery device 300 with an incorrect drug reservoir or container 320.

In an embodiment, system 100 may be configured to block the insertion of all drug reservoirs 320 other than a given drug reservoir 320 for which the drug delivery 300 device is intended. In another embodiment, the system 100 may be configured to only block drugs that are considered dangerous for using with the device 300 (e.g. a short-acting drug could be fitted into a device intended for long-acting insulin, or a low-concentration drug could be fitted into a device intended for a high-concentration drug, but not vice versa).

The method and system may also react to an identified drug reservoir 320 and take an appropriate action during a dose selection phase (i.e. when a user is selecting a dose). For instance, system 100 may be configured to control dose selection based on the identified drug reservoir 320. Similar to preventing loading of an incorrect drug reservoir 320, system 100 may be configured to prevent dose selection when the identified drug reservoir 320 is not intended for use with the drug delivery device 300. System 100 may, for instance, trigger a latch, such as latch 116, that prevents a user from setting a dose when an incorrect reservoir 320 is loaded in the drug delivery device 300.

Other examples of controlling dose selection are possible as well. For instance, system 100 may control dose selection based on the identified drug reservoir 320 by setting or enforcing a maximum dose. The drug reservoir 320 may contain a drug that should only be dosed in small increments (e.g. 20 units or less). Thus, the system 100 may be configured to prevent a user from setting a dose greater than 20 units when such a drug reservoir 320 is inserted in the drug delivery device 300. As another example, system 100 may control dose selection based on the identified drug reservoir 320 by setting or enforcing a minimum dose.

As yet another example, system 100 may control dose selection based on the identified drug reservoir 320 by controlling the dosing frequency. For instance, if a drug should not be dosed more than once a day, after a user injects a dose, the system 100 may be configured to lock the drug delivery dose setting mechanism out for a 24-hour period. For example, the system 100 may activate the electronic latch 116 to prevent dose setting for the 24-hour period.

The method and system may also react and take an appropriate action during the dispensing phase (i.e. when a user dispenses the drug). The system 100 may be configured to control dispensing of the drug based on the identified drug reservoir 320. For example, similar to preventing loading of an incorrect drug reservoir 320 and dose selection with an incorrect reservoir 320, system 100 may be configured to prevent dispensing when the identified drug reservoir 320 is not intended for use with the drug delivery device 300.

As another example, controlling dispensing of the drug based on the identified drug reservoir 320 may include controlling a dispense speed and/or a required dispense force. Controlling a dispense speed and/or a required dispense force may be beneficial for various reasons. For example, certain drugs may require an increased dispense force due to crystallizing on the bung and/or high viscosity. In such a case, it may be beneficial to inject the drug slowly in order to reduce the force needed by a motorized drive. Further, in such a case, injecting such a drug may be painful for the user, so slower injection may reduce any pain. As another example, one other reason to control speed/force is to detect abuse loads, e.g. to detect blockages it is necessary to know what force is 'normal' for a given drug at a given speed.

As yet another example of identifying information related to drug reservoir 320, system 100 may be used to identify the time that has elapsed since drug reservoir 320 was loaded into the drug delivery device 300. For example, the time at which the cartridge holder latch was last operated could be recorded into memory in the device 300, or on the drug reservoir 320.

System 100 may also be used as part of a 'closed loop' drug pump. The pump would detect the patient's needs, for example using a Blood Glucose Monitor, and then dispense the correct amount of drug, for example insulin. The system 100 may be able to vary the volume of drug dispensed to allow for variables such as drug concentration, or drug type.

Rather than system 100 being disposed in or on the drug delivery device 300, system 100 may be a stand-alone device, such as a scan gun or used for identifying information related to drug reservoirs 320 or a drug-identification base station. The stand-alone system may be used by, for example, a patient or medical staff personnel, or a drug manufacturer in order to identify information related to drug reservoirs 320. Such a stand-alone device may be used for a variety of reasons. For example, the stand-alone system may be used to aid with storage or shipping of drug reservoirs 320. As a particular example, the system 100 may be used to identify the expiration date of the drug reservoir 320. As another example, system 100 may be used to identify required storage conditions for the drug reservoir 320. It may also be possible to record storage conditions experienced by a cartridge or drug reservoir 320, e.g. with a temperature sensitive label, and for this information to be read by the device.

The circuit 122 or circuits of the coded material 120 may be designed and manufactured in any way currently known in the art or later developed. In given embodiments of the present disclosure, a standard circuit may be manufactured, and the standard circuit can then be modified in various ways based on the information the modified circuit is intended to represent. This practice of manufacturing a standard circuit and, thereafter modifying it may be particularly beneficial or useful for coding small batches of drug reservoirs 320.

Figure 8A:
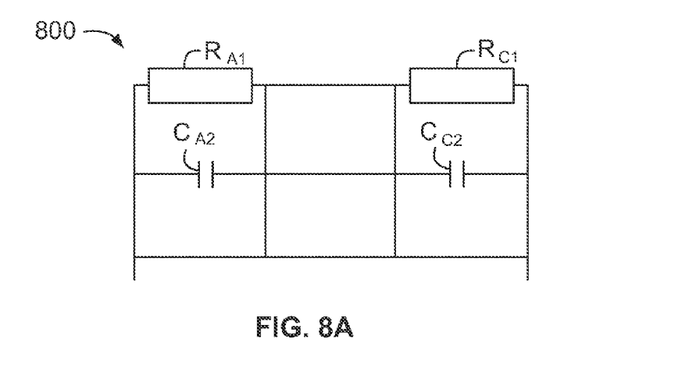
FIG. 8A illustrates an example standard circuit.
Figures 8B, 8C:
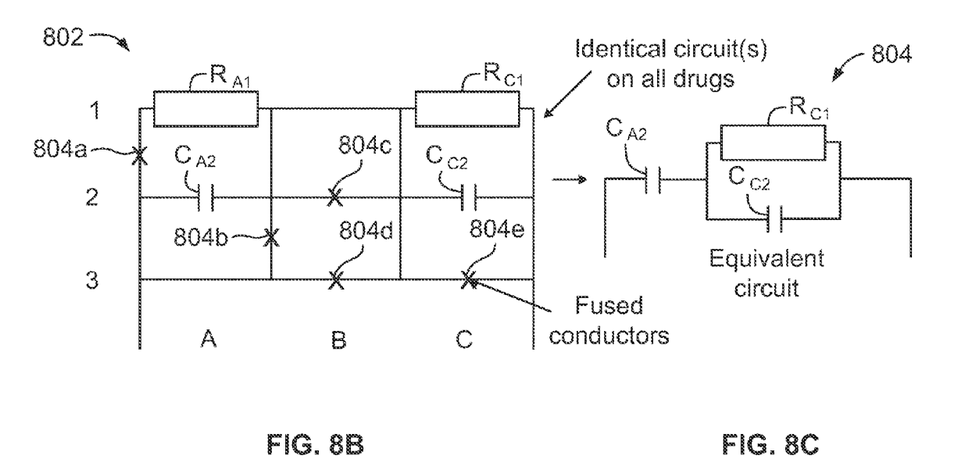
FIG. 8B illustrates an example modified version of the standard circuit of FIG. 8A, where the modified version may serve to indicate information about a given drug reservoir.
FIG. 8C illustrates an equivalent circuit of the modified standard circuit of FIG. 8B.

As one example of a modification, some conductors may be fused or cut to indicate a type of a drug or other information about a drug reservoir 320. FIGS. 8A-*c* depict such an example. FIG. 8A depicts a standard circuit 800, and FIG. 8B depicts a modified circuit 802. As shown, circuit 802 has fused conductors 804*a-e*. The fused conductors 804*a-e* cause circuit 802 to be the equivalent of the circuit 804 shown in 8C. Fusing conductors in different ways will create circuits having different properties. It should be appreciated that many examples and equivalent circuits are possible.

The standard circuit 800 may comprise of building blocks of circuits, or a number of separate circuits. In an example, a mechanical feature on the drug reservoir 320 would be in a different position relative to the circuits for each different drug, and the drug delivery device 300 would recognize the drug by where the circuits are connected to the device 300. Two or more of the connectors might form a short-circuit, which would bypass part of the circuit 800.

Figures 9A, 9B:
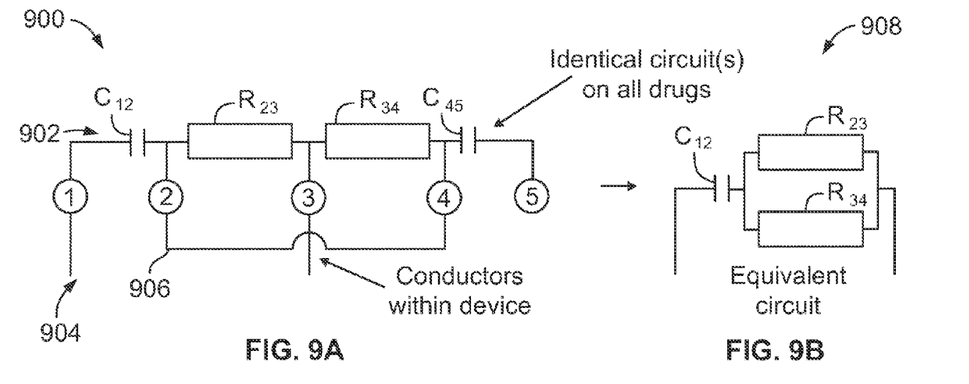
FIG. 9A illustrates an example of a detector feature having a plurality of connectors connected to a coded material having a circuit.
FIG. 9B illustrates an equivalent circuit of the detector feature and coded material of FIG. 9A.

In this system, varying connectors and conductors in the device 300 could combine building blocks in series or in parallel. Such an example is shown in FIGS. 9A-B. FIG. 9A illustrates an example of a detector feature 904 having a plurality of connectors 1 to 5 connected to a coded material 900 having a circuit 902 comprising two capacitors $C_{12}$, $C_{45}$ and two resistors $R_{23}$, $R_{34}$. In the device 300, there are connectors at positions 1 to 4, but not at position 5, and connectors 2 and 4 are connected together by a circuit 906 within the device 300. This arrangement of connectors 1-5 in the device 300 causes the circuit 902 of the coded material shown in FIG. 9A to be the equivalent of the circuit 908 shown in FIG. 9B.

Figure 10A:
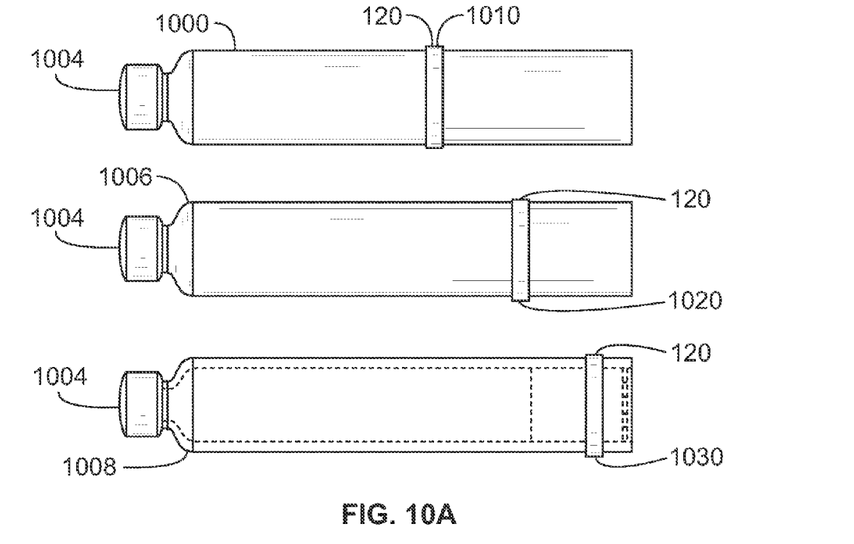
FIGS. 10A and 10B illustrate examples of possible positions of coded material on a drug reservoir.
Figure 10B:
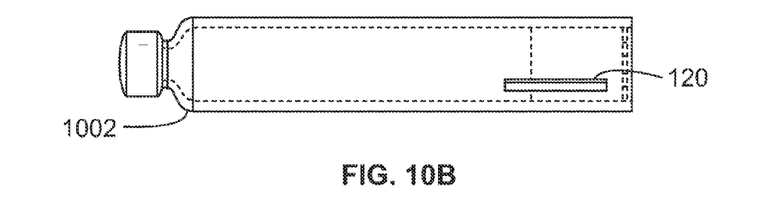

In an embodiment, the coded material 120 having the circuit 122 may be applied around the full circumference of the drug reservoir. For example, as shown in FIG. 10A, coded material 120 is applied around the full circumference of drug reservoir 1000. In such an embodiment, the orientation of the drug reservoir 1000 as it is loaded is not important. In other arrangements, the coded material 120 may be a discrete area, (e.g. a strip) of material that is not disposed around the full circumference of a reservoir, such as the strip of coded material 120 on drug reservoir 1002 shown in FIG. 10B.

As mentioned above, position of the coded material 120 relative to a standard feature may be used to identify information about the drug reservoir 1000, 1002. As such, system 100 may be further configured to detect the position of the coded material 120. As an example, with reference to FIG. 10A, system 100 may be configured to detect the position of the coded material 120 relative to the axial length from the distal end 1004 of a drug reservoir. 1000 For instance, coded material 120 at position 1010 may indicate to system 100 that the drug reservoir is reservoir 1000. Coded material 120 at position 1020 may indicate to system 100 that the drug reservoir is a reservoir 1006. Coded material 120 at position 1030 may indicate to system 100 that the drug reservoir is a reservoir 1008. If position is used for the coding, the position on different drug reservoirs 1000, 1002, 1006, 1008 is preferably far enough apart (e.g. 10 millimeters (mm)) so that the drugs may be accurately distinguished from one another.

In an alternative embodiment, the coded material 120 may be aligned with the connector(s) 104, 104*a-c* of system 100 when a drug reservoir is loaded. Alignment may be accomplished in various manners, such as aligning the coded material 120 with the connector 104 of system 100 using a mechanical protrusion or indentation in the drug reservoir to force alignment. Alignment may be of particular benefit when the arrangement of the connectors 104*a-c* of the detector feature 100 is important when connected to the coded material 120. However, in other situations, alignment may not be necessary, such as in the case where the connector 104 is a contactless connector.

In an embodiment, where multiple areas of coding are applied, the multiple areas of coding may be read during insertion into the reading apparatus, so that only one connector 104 is needed. For example, a reservoir may have three areas of coding material 120, such as a coded area indicating a storage condition, a coded area indicating the type of drug, and a coded area indicating expiration date. These coded areas may be displaced vertically 5 mm apart from one another. As a drug reservoir is inserted into the system 100, the system 100 may communicate with the coded areas at each 5 mm interval and may identify electrical property or properties of all three coded materials 120.

The present disclosure results in a number of advantages. For example, the present disclosure results in a user-friendly system that identifies information related to a drug reservoir automatically by electronic means. There are also quite a large number of different coding materials that may be used. Consequently, with the disclosed coding scheme, a large number of medicaments can be distinguished from one another. In addition, with the disclosed coding scheme, if a user attempts to load an incorrect reservoir, the user may be alerted at an early stage of the assembly step that the user is attempting to load in incorrect reservoir and, hence, attempting to possibly use a wrong medicament.

Additionally, the disclosed system and method may make drug reservoirs difficult to counterfeit. The disclosed system and method may beneficially reduce tampering and/or counterfeiting of drug reservoirs. Because such reservoirs with coded materials may be difficult to tamper with, they may also reduce the risk of counterfeiting: i.e. making it more difficult for counterfeiters to provide unregulated counterfeit medicament carrying products.

In certain embodiments, an additional benefit is that no electrical contacts are needed. Another benefit is that the disclosed method and system provides a low-cost coding scheme for coding drug reservoirs and providing information about drug reservoirs.

Although aimed primarily at the insulin market, the present disclosure may apply to other drugs. The present disclosure may apply to various devices, including the following examples; an injector pen with a cartridge (e.g. 3 ml cylindrical glass cartridge) and a separate holder as illustrated in FIG. 3A. The present disclosure may also apply to an injector pen with a cartridge (e.g. 3 ml cylindrical glass cartridge) non-removably retained in a holder, so that the holder will be disposed of with the primary pack, and to an injector pen where the primary pack attaches directly to the pen, e.g. an injection-moulded polymer cartridge.

Figure 11:
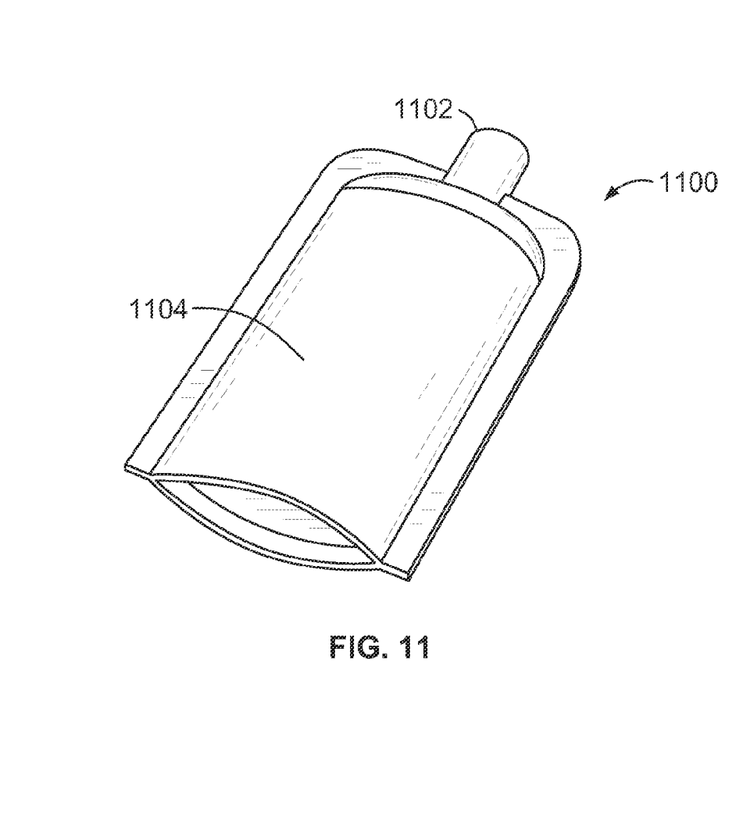
FIG. 11 illustrates an alternative reservoir.

In other applications, the present disclosure may apply to any drug delivery device, with any type of primary pack, e.g. inhaler, pouch. For example, coding features such as a coded material 120 may be added to a pouch, such as the pouch 1100 illustrated in FIG. 11. In an embodiment, coding features are added to port 1102. However, coded material 120 may also be added to the body 1104 of the pouch 1100.

Figure 12:
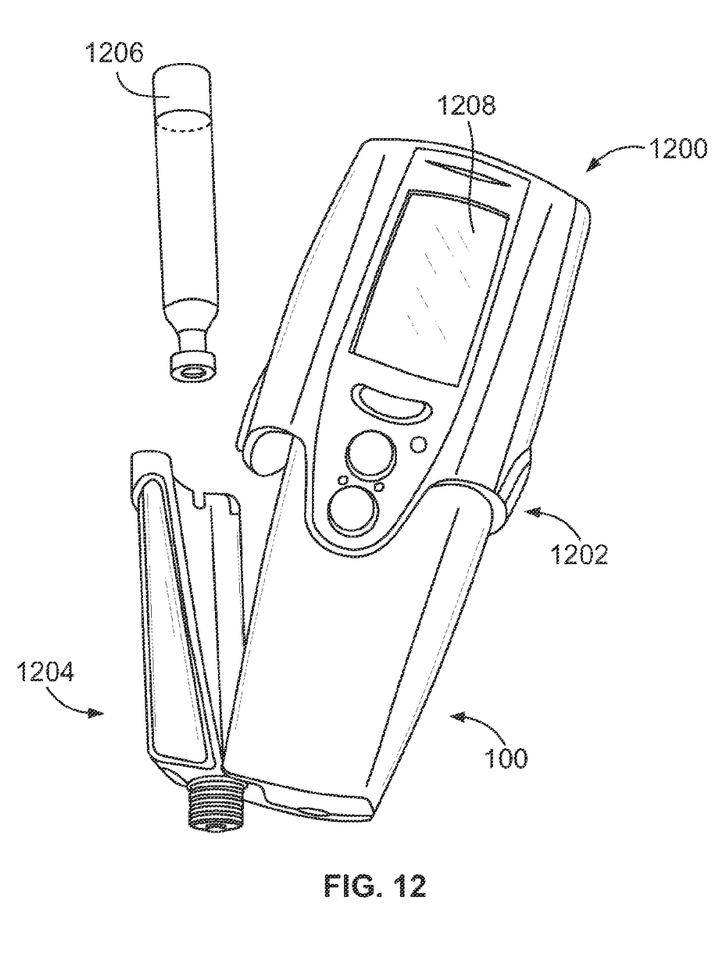
FIG. 12 illustrates another example drug delivery device that may include the system of FIG. 1.

Another example of a device that may include system 100 is shown in FIG. 12. Referring to FIG. 12, there is shown a drug delivery device 1200, which is a credit-card-shaped drug delivery device. Drug delivery device 1200 comprises a body 1202. Body 1202 includes a cartridge retaining portion 1204 into which a cartridge 1206 may be inserted. When cartridge 1206 is inserted, system 100 may detect information related to the coded material 120 of the cartridge. Device 1200 also includes a screen 1208, which may display information related to the cartridge 1206 to the user of the device 1200. It should be understood that system 100 may be used in various other devices as well.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A method of determining information related to a drug reservoir, the method comprising:
   providing a medical delivery device, the device comprising
   a drug reservoir holder operable to receive a drug reservoir,
   a detector, and
   the drug reservoir,
   the detector determining an electrical property related to a coded material for the drug reservoir, wherein the coded material comprises at least one circuit, and, based at least on the determined electrical property, determining information related to the drug reservoir, wherein, when the drug reservoir is inserted in the drug delivery device, the method further comprises:
   controlling dose selection based on the identified drug reservoir, wherein controlling dose selection based on the identified drug reservoir comprises at least one of preventing dose selection when the identified drug reservoir is not intended for use with the drug delivery device, and setting a maximum dose or setting a minimum dose when the identified drug reservoir is intended for use with the drug delivery device, and
   controlling dispensing of the drug based on the identified drug reservoir, wherein controlling dispensing of the drug based on the identified drug reservoir comprises preventing dispensing of the drug when the identified drug reservoir is not intended for use with the drug delivery device and, controlling at least one of an adjustable dispense speed of the device or an adjustable dispense force of the device when the identified drug reservoir is intended for use with the drug delivery device, wherein controlling the at least one of the adjustable dispense speed or the adjustable dispense force comprises selecting, based on a medicament in the identified drug reservoir, at least one of a desired dispense speed or a desired dispense force.

2. The method of claim 1, wherein at least one component of the at least one circuit is printed onto the drug reservoir.

3. The method of claim 1, further comprising determining a second electrical property of the at least one circuit, and, based on the second property, determining information related to the drug reservoir.

4. The method according to claim 1, wherein the detector feature comprises an oscillator, and wherein the determined electrical property comprises at least one of a resonant frequency of the at least one circuit and an attenuation of the at least one circuit.

5. The method according to claim 1, wherein the at least one circuit comprises a low-pass filter or a high-pass filter, and wherein the determined electrical property comprises at least one of a frequency passed and a frequency blocked.

6. The method according to claim 1, wherein the detector comprises one or more electrical connectors for communicating with the coded material, wherein the electrical connector is a contact or a contactless electrical connector.

7. The method according to claim 1, wherein the information related to the drug reservoir is information selected from the group consisting of drug type, drug concentration, a manufacturing date of the reservoir, an expiration date of the drug, and a storage condition of the drug.

8. The method according to claim 1, wherein the step of determining information related to the drug reservoir is performed as a user attempts to load the drug reservoir in a drug delivery device, and wherein the method further comprises:

based on the determined information, identifying the drug reservoir and/or, based on the determined information, determining that the drug reservoir is not intended for use with the drug delivery device.

9. The method of claim 8, further comprising displaying an indication that the drug reservoir is not intended for use with the drug delivery device.

10. The method of claim 8, further comprising preventing insertion of the drug reservoir into the drug delivery device, wherein preventing insertion of the drug reservoir comprises activating an electronic latch that prevents insertion of the drug reservoir.

11. The method according to claim 8, wherein, when the drug reservoir is inserted in the drug delivery device, the method further comprises:

controlling dose selection based on the identified drug reservoir, wherein controlling dose selection based on the identified drug reservoir comprises controlling the dosing frequency.

12. A medical delivery device comprising:

a drug reservoir holder operable to receive a drug reservoir;

a detector configured to be operable (i) to determine an electrical property related to a coded material for the drug reservoir, wherein the coded material comprises at least one circuit and, (ii) based at least on the determined electrical property, to determine information related to the drug reservoir, wherein the detector comprises a processor and data storage comprising instructions executable by the processor, wherein, when a user attempts to load the drug reservoir into the drug delivery device, the instructions are further executable by the processor to, based on the determined information, identify the drug reservoir, determine whether the drug reservoir is intended for use with the drug delivery device, and control dose selection based on the identified drug reservoir, wherein controlling dose selection comprises (i) preventing dose selection when the identified drug reservoir is not intended for use with the drug delivery device and (ii) controlling at least one of an adjustable dispense speed of the device or an adjustable dispense force of the device and setting a maximum dose or a minimum dose when the identified drug reservoir is intended for use with the drug delivery device, wherein controlling the at least one of the adjustable dispense speed or the adjustable dispense force comprises selecting, based on a medicament in the identified drug reservoir, at least one of a desired dispense speed or a desired dispense force.

13. The medical delivery device of claim 12, further comprising:

a display configured to display at least a portion of the information related to the drug reservoir.

14. The medical delivery device according to claim 12, wherein the detector comprises an electrical connector for communicating with the coded material, and wherein the electrical connector is a contact or a contactless electrical connector.

15. The medical delivery device according to claim 12, wherein the instructions are further executable by the processor to one or more of:

display an indication that the drug reservoir is not intended for use with the drug delivery device, and prevent insertion of the drug reservoir into the drug delivery device.

16. The medical delivery device of claim 12, wherein at least one component of the at least one circuit is printed onto the drug reservoir.

17. The medical delivery device of claim 16, wherein the detector comprises an oscillator, and wherein the determined electrical property comprises at least one of a resonant frequency of the at least one circuit and an attenuation of the at least one circuit.

18. The medical delivery device of claim 16, wherein the at least one circuit comprises a low-pass filter or a high-pass filter, and wherein the determined electrical property comprises at least one of a frequency passed or blocked.

* * * * *